United States Patent [19]
Romare

[11] Patent Number: 6,114,597
[45] Date of Patent: Sep. 5, 2000

[54] ABSORBENT PRODUCT FOR RECEIVING BODY FLUIDS

[75] Inventor: Anette Romare, Mölndal, Sweden

[73] Assignee: SCA Hygiene Products AB, Gothenburg, Sweden

[21] Appl. No.: 09/029,364

[22] PCT Filed: Aug. 29, 1996

[86] PCT No.: PCT/SE96/01061

§ 371 Date: Feb. 24, 1998

§ 102(e) Date: Feb. 24, 1998

[87] PCT Pub. No.: WO97/09014

PCT Pub. Date: Mar. 13, 1997

[30] Foreign Application Priority Data

Sep. 6, 1995 [SE] Sweden ................................ 9503066

[51] Int. Cl.$^7$ ................................................ A61F 13/15
[52] U.S. Cl. .............. 604/378; 604/385.01; 604/385.24; 604/387; 604/389
[58] Field of Search ................. 604/378, 385.1, 604/385.2, 386, 387, 389

[56] References Cited

U.S. PATENT DOCUMENTS

| | | |
|---|---|---|
| 3,183,909 | 5/1965 | Roehr . |
| 4,022,210 | 5/1977 | Glassman ................................ 604/389 |
| 4,285,343 | 8/1981 | McNair . |
| 4,425,130 | 1/1984 | DesMarais ................................ 604/389 |
| 4,605,405 | 8/1986 | Lassen . |
| 4,608,047 | 8/1986 | Mattingly . |
| 4,804,380 | 2/1989 | Lassen et al. . |
| 5,057,096 | 10/1991 | Faglione . |
| 5,236,428 | 8/1993 | Zajackowski ........................ 604/385.2 |
| 5,507,735 | 4/1996 | Van Iten ............................... 604/385.1 |
| 5,618,283 | 4/1997 | Yamamoto ............................... 604/390 |
| 5,814,037 | 9/1998 | Coates ..................................... 604/393 |

FOREIGN PATENT DOCUMENTS

| | | |
|---|---|---|
| 0 067 465 A2 | 12/1982 | European Pat. Off. . |
| 0 130 848 | 1/1985 | European Pat. Off. . |
| 0 134 086 A1 | 3/1985 | European Pat. Off. . |
| 0 425 026 A2 | 5/1991 | European Pat. Off. . |
| 455 668 | 8/1988 | Sweden . |
| WO 90/04956 | 5/1990 | WIPO . |

*Primary Examiner*—Dennis Ruhl
*Attorney, Agent, or Firm*—Burns, Doane, Swecker & Mathis, L.L.P.

[57] ABSTRACT

The invention relates to an absorbent product such as a sanitary napkin, a panty liner, an incontinence protector, or the like, intended during use to be arranged in the crotch region of a user in order to collect and absorb discharged body fluids, and which has means for fastening inside a pair of underpants. The product has a principally elongated shape with a longitudinal center-line and a transverse center line and comprises an upper part intended during use of the product to be facing towards the user and a lower part intended during use of the product to be facing away from the user. The two parts are mutually joined and each have a front part, intended during use of the product to be facing forwardly towards the abdomen of a user, as well as a rear part intended during use of the product to be facing rearwardly towards the behind of the user. The upper part and the lower part further each have a front transverse edge, a rear transverse edge as well as two longitudinal side edges extending between the two transverse edges. The principal distinguishing characteristic of the invention is that the upper part and the lower part are mutually joined only at the acquisition zone of the product, which is the region of the product which is intended to first be wetted by body fluid, wherein the upper part around the whole of the periphery of the acquisition zone is free from connections to the lower part.

21 Claims, 2 Drawing Sheets

ABSORBENT PRODUCT FOR RECEIVING BODY FLUIDS

BACKGROUND OF THE INVENTION

The present invention relates to an absorbent product such as a sanitary napkin, a panty liner, an incontinence protector, or similar, intended during use to be placed in the crotch region of a user in order to collect and absorb emitted body fluids, which has means for fastening inside a pair of under-pants, which product comprises an upper part intended during use of the product to be facing towards the user, as well as a lower part intended during use of the product to be facing away from the user.

Products of this type are of fairly small size and are intended to be worn inside a pair of underpants and, during use, to be held in contact against the body of the user by pressure from the underpants. Furthermore, this type of product usually has a fastening means in the form of self-adhesive glue, which allows fastening inside the underpants. Other types of fastening means are also known, such as different sorts of friction coatings and mechanical fastening means, such as press-studs and hook and loop surfaces.

A significant problem with the previously known products is that they are greatly deformed during use, because they are subject to compression between the thighs of the user. The deformation effect when the user moves is especially significant. When an absorbent product is compressed in the transverse direction, the surface directly available for receiving fluid naturally diminishes. This has the consequence that a large number of conventional absorbent products of this type, to an unsatisfactorily large extent, are incapable of preventing soiling and staining of the leg edges of the underpants of the user.

In order to reduce the leakage which occurs through the absorbent product being compressed between the legs of the user, it has become normal to equip the absorbent products with special fastening flaps. For example, from SE 455,668; U.S. Pat. No. 4,285,343; EP 130,848; EP 134,086; and U.S. Pat. No. 4,608,047, it is known to provide sanitary napkins with flexible side flaps or wings extending from the longitudinal side edges. Such side flaps are intended, during use, to be folded around the leg edges of the underpants of the user, and be fastened to the underside of the underpants. The side flaps themselves form a protection against side edge leakage and soiling of the underpants. Furthermore, the deformation of the absorbent body of the napkin is counteracted through the napkin being anchored on the side edges of the underpants and during use being held stretched out between these.

A considerable drawback with equipping absorbent products with such fastening flaps is, however, that many users regard the fact that, during use, the fastening tabs are visible outside the underpants as embarrassing. This means that even sanitary napkins or panty liners with such fastening flaps, for example, cannot be used when the user wears a swimsuit.

Another disadvantage with fastening flaps is that they are comparatively difficult to handle and require many manipulations to be placed in the right way in a pair of underpants. Furthermore, especially with fastening flaps which extend along a considerable length of the side edges of the absorbent product, it can be difficult to fold the fastening flaps around the curved leg edges of the underpants, without chafing and unaesthetic folds arising in the fastening flaps.

Another problem with the use of the known absorbent products is that the forces occurring when the user moves not only give rise to unwanted deformation of the product, but also cause the material in the underpants of the user to be compressed or to be stretched out during the movements. Because the product is fastened in the underpants, it is naturally influenced by movements of the underpants. The user may feel that the product chafes and irritates the skin in the crotch region. Even if the user does not feel any direct physical discomcort, the movements of the product can give rise to psychological discomfort, because the user is continually reminded by the movements of the product of its presence in the underpants, and the wearing of the product is therefore felt to be especially conspicuous.

From a functional point of view, it is a serious problem that the absorbent product can move with the underpants in relation to the user's body, as the product in this manner can temporarily adopt an incorrect position in relation to the body, even if the product is correctly placed inside the underpants. Furthermore, the movements of the underpants can cause gaps to arise between the product and the user's body, through which body fluids can escape. Movement of the product with respect to the user's body during use is especially unsuitable and undesirable in connection with those products which have been given a special shape in order to better conform the anatomy of the user, or in which the absorption capacity has been optimized with the requirement that the main part of the body fluid which is to be absorbed impinges on the product within a limited predetermined region of the product. It is, for example, normal to equip sanitary napkins with a raised part intended to be in contact with the user's body around the vaginal opening, in order to immediately collect and absorb discharged fluids. Furthermore, incontinence protectors for male users are often formed with a three-dimensional shape which completely or partially surrounds the genitals of the user. There is furthermore a certain risk that the sliding forces which are generated between the product and the underpants during the movements of the user cause the product to be loosened from the underpants. There is obviously then a risk that the product adopts an incorrect position in the underpants, whereby leakage occurs.

In EP 67,465 and EP 425,026, sanitary napkins are described which are made of an upper and a lower part which are mutually joined along one or both of the transverse end edges of the sanitary napkin and in this way have a certain freedom of movement relative to one another. This freedom of movement is sometimes not enough and the two parts in the known sanitary napkins can be influenced during use to an excessively high degree by the movement of each other for total comfort and security against leakage to be achieved.

The absorbent products can also be deformed longitudinally when they are used, since they are bent or flexed to conform to the body of the user inside the underpants. During such bending, transverse creases appear in the surface layer of the products and, sometimes, creases and cracks in the absorbent material inside the product also occur. These transverse creases and cracks serve as fluid-conducting channels and can in unfortunate cases conduct fluid out past the longitudinal side edges of the products with leakage as a consequence. This problem is especially obvious in incontinence protectors which often must be able to receive relatively large amounts of fluid discharged in a short space of time. If, on that occasion, there are creases in the surface layer of the incontinence protector, then fluid can run out of the incontinence protector before it has been able to be absorbed by the absorption material in the protector. Another situation where this type of leakage is annoying is during night use of sanitary napkins. When the user is lying down, relatively large amounts of menstruation blood can accumulate inside the womb and can be discharged quite suddenly when the user turns in her sleep, or when she awakes and gets up. Leakage of blood is naturally especially irritating, because, apart from the disturbed sleep, it also causes staining of clothes and bed linen which may have to be thrown away.

Another type of night leakage is due to fluid running out along the body of the user, for example in the groove between the buttocks, and in this way leaking out past the absorbent body. In order to prevent this type of leakage, it has been suggested in U.S. Pat. No. 4,804,380 to equip the sanitary napkin with a type of hump which should fit into the space behind the vaginal opening and in this way stop fluid from running back on the user. Another way of solving the problem with rearward leakage is to equip a sanitary napkin with a sort of tampon which, in a similar fashion, is intended to prevent fluid from running back. Such a sanitary napkin is described in WO 90/04956.

These products are strongly influenced, however, by the movements and tensile forces which occur in the underpants of the user during use, whereby they are easily displaced when the user moves and the material in the underpants is stretched or compressed. Furthermore, they are experienced by many users as being uncomfortable to wear, since during movement they can chafe and irritate the sensitive skin in the crotch of the user.

With the present invention, however, an absorbent product of the type described in the introduction has been achieved, in which the problem with leakage and deformations known in connection with earlier such products has been diminished considerably. An absorbent product made according to the invention is distinguished, firstly, in that the upper part and the lower part are mutually joined only at the acquisition zone of the product, which is the region of the product which is intended to first be wetted by body fluid, wherein the entire upper part external to the acquisition zone is free from connections to the lower part.

Other features and embodiments are detailed in the appended claims.

SUMMARY OF THE INVENTION

In accordance with the invention, by designing an absorbent product comprising two parts, of which the lower part is firmly anchored inside the underpants of the user, and the upper part only has a comparatively little region in which it is fastened to the lower part, and in this way indirectly fastened to the underpants, a large amount of mutual movement between the two parts is achieved. In this way, it is possible to provide an absorbent product which is securely fastened in the underpants and which nevertheless has a high comformity to the body of the user and anatomically correct fit with consequently high leakage security and comfort during use.

It is further possible to shape the parts comprising the product in such a way that the upper part is completely adapted to the shape of the user's body and built up in order to collect all the emitted body fluid in the best possible way. The lower part can, without reference to the anatomy of the user, be made of such material and with such a shape that it can easily be fastened inside a pair of underpants and thereby follow the shape and movements of the underpants.

In a preferred embodiment, the upper part of the product has in the front part a bowl shape which closes around the genitals of the user. The bowl shape is suitably achieved by some type of elastic means, for example elastic threads, bands, or the like, which are arranged at least along the longitudinal side edges of the upper part, but advantageously also along its transverse front edge. At the rear, the upper part is preferably narrowed and suitably equipped with some form of hump which fits between the buttocks of the user and, in this way, prevents rearward leakage, for example during night use of the product. Alternatively, the rear part of the upper part can have a means in the form of a compression line, a slot or similar, which contributes to the product during use moulding itself so that it forms a hump which fits between the buttocks of the user. For the sake of comfort, the back part of the upper part should not be longer than required, so that it precisely reaches the space between the buttocks behind the genitals of the user. On the other hand, the lower part should extend further backwards, in order to collect any possible body fluid which leak out past the rear edge of the upper part.

The lower part of the product preferably has an essentially reversed shape compared with the upper part, and has therefore a wider rear part and a narrower front part. The lower part is, however, preferably essentially flat. The lower part is fastened in a conventional manner in a pair of underpants, for example by means of glue, friction coatings, hook and loop surfaces, press-studs or the like.

If so desired, it is also naturally possible to equip the lower part with fastening flaps which extend outwards from the longitudinal sides. Such an embodiment is, however, not absolutely necessary to ensure high leakage resistance in the product. It is particularly advantageous that the lower part of the product be fastened to the underpants over essentially the whole of its surface facing towards the underpants. In this manner, a total fitting of the lower part to the underpants is more or less achieved. Alternatively, the lower part can be equipped with fastening means which permit fastening along essentially the whole periphery of the lower part. The lower part should be comparatively thin, preferably not over 2 mm, should be flexible and can advantageously also have a certain stretchability. In this way, a lower part can be achieved, which follows the shape and movements of the underpants extremely well without it coming loose or having undesirable creases or ruptures.

When the lower part is fastened to the underpants over essentially the whole of the surface which is in contact with the underpants, the lower part during use will to a large degree follow the movements of the underpants. Because the connection between the upper part and the lower part is only in a very limited region, and furthermore, is in the region in which the shear forces between the two parts are least, the lower part is only marginally influenced by the movements of the upper part. In this way, the lower part is very securely anchored in the underpants when the product is used.

In a corresponding manner, the upper part is only influenced to a small degree by the movements in the underpants and of the lower part of the product. Deformations of the upper part as well as the lower part are therefore considerably smaller than the deformations of the absorption body in conventional absorbent products. If, however, the upper part is compressed between the legs of the user, and in this manner is deformed in such a way that fluid leaks out past the edges of the upper part, leakage is prevented through such fluid being collected and absorbed by the lower part. Because the upper part is hardly influenced by movements of the underpants, the risk for chafing of the skin of the user and other discomfort caused by movements of the product during use are almost completely eliminated.

The joining region between the upper part and the lower part of the product lies essentially in and around the acquisition zone of the product. By this it is meant the area of the product which is intended to first be wet by discharged body fluid. Depending on the anatomy, body position and movements of the user, as well as the fit of the underpants and the placement of the product inside the underpants, the actual positioning of the acquisition zone can, in practice, vary somewhat. However, it is usual for the acquisition zone to be placed along a longitudinal centre line through the product and to be displaced somewhat forward from a transverse centre line through the product. During night use of the absorbent product, when the user lies down, the actual acquisition zone is, however, often shifted to the rear of the product. Under all circumstances, the acqusition zone should be within a region which is placed at a distance which is at least ¼ of the total length of the product from the front and rear transverse edges of the product. In a corresponding manner, the distance between the acquisition zone and the longitudinal side edges of the product should be at least ⅛ of the width of the product.

The joining region is the region of the product in which controlled transfer of fluid can take place between the upper part and the lower part of the product. This is achieved, for example, by the upper part inside this region having one or more through-openings, or liquid permeable regions. Besides, the surface of the upper part of the product which is facing towards the lower part can be essentially impermeable for fluids, in which manner the main absorption will take place in the upper part, as well as in the part of the lower part which is lying immediately adjacent the connecting region. It is advantageous if the connection between the upper part and the lower part has a certain elasticity, so that the transfer of forces between the underpants and body of the user should be as small as possible during use.

Because the connecting region is limited so as to essentially correspond to the acquisition zone of the product, the front part of the upper part as well as its rear part and longitudinally extending side edges are free from connections to the lower part. In this way the upper part during use can twist around in relation to the lower part, as well as both the front part and the rear part of the upper part being able to separate from the lower part. Twisting of the upper part can take place around an axis perpendicular to the acquisition zone of the product.

Both the upper part and the lower part of the product comprise absorbent material. Furthermore, it is an advantage if both parts of the products are enclosed in a casing which is at least partially liquid-permeable on the side of the product which is intended during use to be facing towards the user. The part of the product which during use is in direct contact with the underpants of the user, or which can come into such contact, should in general be impermeable to fluids. It is, however, from a point of view of comfort, advantageous if the surface of the product which faces the underwear has a certain air and vapour permeability. In order to direct the liquid flow between the upper and lower parts of the product, the liquid permeability of the surface of the upper part which is facing away from the user during use can be different in different regions. For example, it can be preferable that the edge parts of the upper part are liquid-impermeable so that fluid cannot pass from the upper part to the lower part within these parts. Within the edge parts, in the acquisition zone of the product, the liquid transfer between the two parts of the product should be able to take place essentially unobstructed. Therefore, inside the acquisition zone, the surface of the upper part facing towards the lower part should have a liquid permeability which is as high as possible. The transition between areas of different liquid permeability can be sudden, or can occur gradually.

The upper part of the product is intended to collect and transfer liquid to the lower part, where the liquid can be absorbed and contained at a distance from the body of the user. The absorption capacity in the two parts should be adjusted so that the combined absorption capability is optimal. Fluid which meets the product at its front part should, in the main, be absorbed by the lower part, while the upper part should be suitably dimensioned so that it has the capacity to absorb the main part of the fluid which strikes the rear part of the product. Because the main amount of the discharged body fluid will normally be discharged on the product in its acquisition zone, the absorption capacity in this region should be greater than the absorption capacity at the front part of the product, respectively rear part. It can, however, be desirable to displace the absorption capacity rearwardly on the product on such products which are intended for use by users lying in bed, for example during the night. Products of this type can furthermore, in order to eliminate the risk of rearward leakage, be equipped with a sealing upraised edge along the rear transverse edge of the lower part of the product. Such an edge can be made, for example, from foam plastic, fibre wadding, cellulose pulp fluff or similar, and can be straight or bent. Preferably, the edge is soft and flexible and has a certain resilience capacity, so that during the whole time it is used, it is held pressed into contact with the body of the user by its underpants.

The invention shall be more closely described in the following with reference to the accompanying drawings showing embodiments.

DETAILED DESCRIPTION OF THE INVENTION

Figure 1:
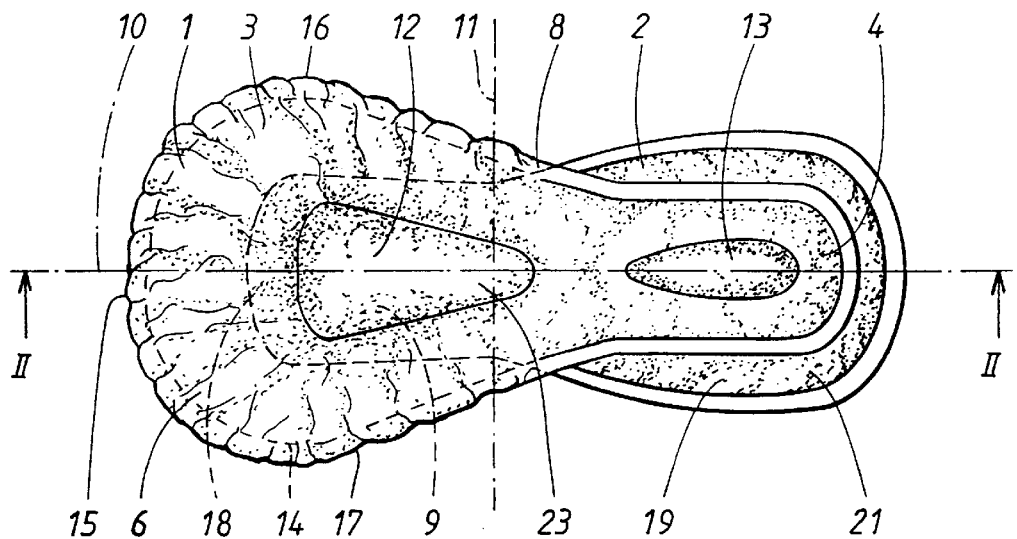
FIG. 1 of the drawings shows a sanitary napkin in accordance with the invention seen from the side which is facing towards the user during use.
Figure 2:
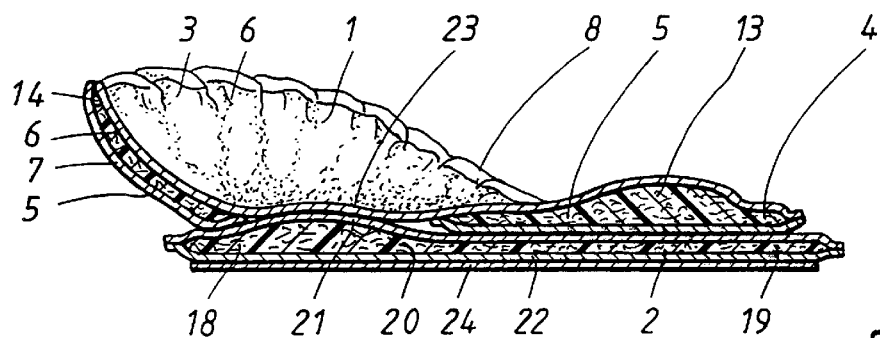
FIG. 2 shows a cross-section along the line II—II through the sanitary napkin in FIG. 1.

The sanitary napkin shown in FIGS. 1 and 2 is formed of an upper part 1, which during use of the sanitary napkin is intended to be facing towards the user, as well as a lower part 2, which during use of the sanitary napkin is intended to be facing towards the underpants of the user. The upper part and the lower part are mutually joined and are displaced in relationship to one another in the longitudinal direction in such a way that the upper part 1 extends beyond the lower part 2 at the part of the sanitary napkin which during use is intended to be facing forwardly, against the stomach of the user, while the lower part 2 extends beyond the upper part 1 at the part of the sanitary napkin which during use is intended to be facing rearwardly on the user.

The upper part 1 can principally be described as being spoon-shaped and has a front part 3 with a rounded shape, which during use is intended to face forwardly on the user, as well as a narrower rear part 4 which during use is intended to extend rearwardly on the user. An upper absorption body 5 is enclosed between two covering layers 6, 7, of which one liquid permeable layer 6 is arranged on the side of the upper part 1 which during use of the sanitary napkin is facing towards the user and a liquid impermeable cover layer 7 is arranged on the side of the upper part 1 which is facing towards the lower part 2 of the sanitary napkin. Both covering layers 6, 7 project beyond the edges of the absorption body, and the projecting parts 8 of the covering layers are mutually joined around the periphery of the absorption body 5, for example by means of gluing, sewing or through welding by heat or ultrasound.

The material of the liquid permeable layer 6 can be of any suitable sort. Examples of normally used liquid permeable covering materials are different kinds of bound, non-woven fibre cloth, so-called non-woven materials, perforated plastic films, nets as well as open-cell or perforated foam material. Different types of laminates, for example laminates of non-woven material and plastic film, can also be used. The liquid impermeable layer 7 is preferably made of a thin plastic film, or of a non-woven material which is made liquid impermeable by coating or treatment with a liquid resistent material. Naturally, other types of liquid barrier material can also be used, for example plastic foam with closed cells, different kinds of liquid barrier laminates etc. In order that the sanitary napkin may feel airy and comfortable to wear, it is preferable that the liquid impermeable layer should have a certain permeability for air and water vapour.

The upper absorption body 5 has in the flat condition essentially the same shape as the upper part, but has a through-opening 9 with the shape of a isosceles triangle with rounded corners. The triangular shape opening 9 is arranged along the longitudinal centre-line 10 of the product, with the point between the equally long edges directed rearwardly on the sanitary napkin. The opening 9 is further arranged essentially symmetrically in the transverse direction along the longitudinal centre-line 10 and is displaced somewhat forwardly on the sanitary napkin in relationship to a transverse centre-line 11 of the sanitary napkin. The opening 9 penetrates the absorption body 5 as well as the liquid impermeable covering layer 7 and its extent corresponds essentially to the acquisition zone 12 of the sanitary napkin, i.e. the region of the sanitary napkin which is intended during use to first be wetted by the emitted body fluids.

At the rear part 4 of the upper part 1, the absorption body 5 is equipped with a drop-shaped hump 13, which is intended during use to sealingly lie against the body of the user behind the vaginal opening of the user and in this way prevent rearward leakage of body fluids. The drop-shaped hump 13 can be shaped from absorbent material such as pulp fluff, foam material, layers of tissue, or absorbent non-woven material. The hump 13 can, however, alternatively be shaped of material with a high resilient capacity, but essentially zero, or comparatively low, absorption capacity. Examples of such materials are plastic foam, bound or unbound fibre waddings or non-woven material. In order to bind possible fluids which reach the hump 13, it can advantageously contain so-called super-absorbent material. By super-absorbent material, it is meant here such materials which can take up and bind fluid in an amount which corresponds to many times the weight of the super-absorbent material. A number of different types of super-absorbent material is known, and they occur in various different physical forms, such as particles, granules, fibres, in the form of non-woven material, as sheets or as foam. Any type whatsoever of super-absorbent and any physical form whatever of it which is found to be suitable for the purpose can be used within the scope of the invention.

The upper part 1 is further equipped with an elastic means 14 which extends beyond the front edge 15 of the upper part 1 and somewhat beyond each of the side edges 16, 17 on the front part 3 of the upper part 1. The elastic means 14 draws together the edge parts 15–17 of the upper part 1 and causes the front part 3 to adopt the shape of a bowl raised up from the lower part around the opening 9 in the upper absorption body 5. The elastic means 14 in the shown example is a thin narrow polyurethane foam band which is glued in place with hot melting glue, so-called hot-melt. Naturally, a range of other types of elastic means can be used within the scope of the invention, such as one or more elastic threads, bands or the like which by means of glueing, or welding by heat or ultrasound are fastened to one or both covering layers or to the upper absorption body. Because the elastic edge will be in contact with the body of the user during use, it is, however, advantageous if the elastic means is of such type and fastened in such a way that it does not cause discomfort in the form of chafing during use.

The lower part 2 of the sanitary napkin has an essentially reversed shape in relationship to the upper part 1. This means that the lower part 2 has a narrow front part 18 and a wide, rounded rear part 19. Just like the upper part 1, the lower part 2 is formed of an absorption body 20 enclosed between two covering layers 21, 22. The covering layer 21 which during use is facing towards the user is liquid permeable, so that any fluid which passes through the upper part 1 shall be able to be absorbed in the lower part 2. The material in the liquid permeable layer 21 of the lower part 2 can be chosen among the materials which have been disclosed as suitable for the liquid permeable layer 6 of the upper part 1.

The whole of the surface of the lower part 2 which is intended to be facing away from the user during use is covered with a liquid impermable covering layer 22. This covering layer 22 can, likewise the liquid impermeable covering layer 7 of the upper part, be made of a plastic film, or of a layer of non-woven or other material, or material laminate which is treated so that it becomes liquid proof. It is in a similar way an advantage if the liquid impermeable covering layer 22 has a certain permeability for air and vapour.

As mentioned earlier, an absorption body 20 is arranged between the two covering layers 21, 22 of the lower part 2. This body is thinner at the end parts 18, 19 of the lower part and thicker at the acquisition zone 12 of the napkin. The absorption body 20 can be made, for example, by air layering of absorption material in a mould, or can be formed from layers of absorption material of the same or different type. Suitable absorption materials are cellulose pulp fluff, different types of band-like cellulose fibre materials which have been cut or folded to the desired shape, super-absorbent non-woven materials of synthetic or natural fibres, super-absorbents, absorbent foam materials, or similar. These absorption materials and way of shaping are also suitable for use during the manufacture of the upper absorption body 5.

The lower part 2 is relatively thin and pliable, as well as having advantageously a certain degree of stretchability. The total thickness of the different parts forming the lower part should at its end parts 18, 19 not exceed approximately 2 mm. At the part of the lower part 2 which is in the acquisition zone 12 of the product, the thickness is, however, somewhat greater and the lower part thus has a hump 23, intended during use to be in contact with the body of the user and to collect the discharged body fluid so near to the body as possible. Such a hump 23 can have a thickness in the order of 1 cm, or more.

The accumulation of absorption material at the acquisition zone 12 of the sanitary napkin coincides in the main with the extension of the opening 9 in the upper part 1 of the sanitary napkin. Both parts 1, 2 of the sanitary napkin are mutually joined in the acquisition zone 12 by means of the liquid permeable covering layer 6 of the upper part 1 being fastened to the liquid permeable covering layer 21 of the lower part 2 in the region of the opening 9 in the upper part 1. This joining together can be made in a number of different ways, for example through glueing, sewing, or welding with heat or ultra sound.

In order to enable the sanitary napkin to be fastened inside a pair of underpants, the liquid impermeable covering layer 22 of the lower part is equipped with a coating 24 of pressure sensitive, self-adhesive glue. The adhesive coating 24 extends over the whole of the surface of the liquid impermeable layer 22 which faces away from the user and in this way ensures an extremely good fastening in the underpants.

During use of the sanitary napkin shown in FIGS. 1 and 2, discharged body fluids are collected in the bowl formed from the upper part 1 around the acquisition zone 12 of the sanitary napkin. The fluid is absorbed below in the lower part 2 through the opening 9 in the upper absorption body 5. In order to achieve this, it is necessary that the absorption body 20 in the lower part 2 of the sanitary napkin in the region of the opening 9 in the upper absorption body 5 has a larger affinity to body fluids than the absorption material in the upper absorption body 5. This can be achieved in a number of different ways, for example through the material in the upper absorption body 5 having larger pores than the material in the lower absorption body 20, or through treatment of the absorption materials so that they have different degrees of hydrophilicity. Different types of absorption materials can also in themselves have different levels of affinity to fluid, whereby the desired liquid transportation direction quite simply can be achieved by a suitable choice of absorption material. The different characteristics of different absorption materials are well known to the man skilled in the art and there is no difficulty in choosing material in such a way that the lower absorption body 20 has a higher liquid affinity than the upper absorption body 5.

In the case that, for some reason, body fluid passes the upper absorption body 5, then it will be directly absorbed by the lower absorption body 20.

If the fluid strikes the sanitary napkin behind the acquisition zone 12, or if fluid runs rearwardly along the sanitary napkin, then, in most cases, it will be absorbed by the absorption material in the upper part 1. The drop-shaped hump 13 at the rear part of the upper part effectively catches fluid which runs backwards and prevents it running further out of the sanitary napkin and giving rise to leakage. Any possible fluid which does not stay in the upper part 1, will instead be absorbed by the lower part 2 of the sanitary napkin which extends out around the rear part 4 of the upper part.

Figure 3:
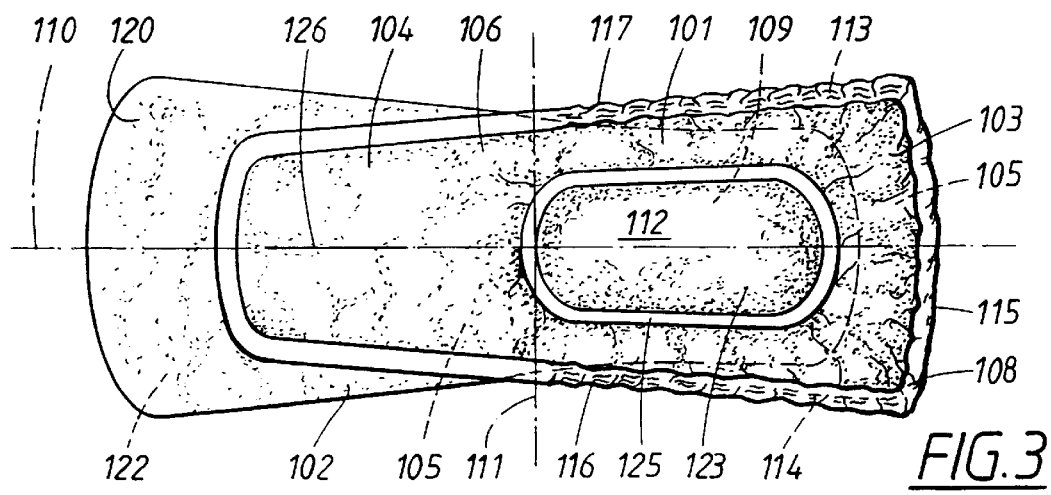
FIG. 3 shows a further embodiment of a sanitary napkin according to the invention seen from the side facing towards the user during use.

The sanitary napkin shown in FIG. 3 comprises an upper part 101, essentially made in the same way as the upper part in FIGS. 1 and 2, as well as a lower part 102. The upper part 101 and the lower part 102 are relatively displaced in relation to one another in a similar manner to the two parts of the sanitary napkin described in FIGS. 1 and 2.

The upper part 101 comprises an upper absorption body 105 contained between a first covering layer 106 and a second covering layer 107, which are mutually joined by projecting covering parts 108 around the periphery of the absorption body 105. The upper part 101 further has a wider front part 103 and a narrowing rear part 104. The first, liquid permeable covering layer 106 is arranged on the side facing towards the user during use of the sanitary napkin and forms in this way a fluid passage into the absorption body 105. The second covering layer 107 is arranged on the side of the upper part 101 which faces towards the lower part 102 and is essentially liquid impermeable. The materials of the two covering layers 106, 107 can, in the same way as shown in connection with the sanitary napkin described in FIGS. 1 and 2, be chosen from among a number of different material and material combinations.

A through oval opening 109 is arranged through the absorption body 105 of the upper part and the second covering layer 107, whereby body fluid can pass down to the lower part of the sanitary napkin through the opening. The opening is so placed laterally and transversally in the sanitary napkin that it essentially corresponds to the acquisition zone 112 of the sanitary napkin.

The upper part 101 of the sanitary napkin is firmly anchored to the lower part 102 in a edge region 125 around the opening 109 in the upper part, for example by being glued, welded, or sewn fast to the lower part 102.

Elastic means 113, 114 are arranged along the side edges 116, 117 on the front part 103 of the upper part. The elastic means 116, 117 extend from the transverse centre line 111 of the sanitary napkin to the front edge 115 of the upper part 101. The elastic means 116, 117 are further applied in a pre-tensioned condition between the two covering layers 106, 107 by means of glueing, welding, or by other means. When the pre-tensioning is released, the elastic means 116, 117 bend the front part 103 of the upper part 101 in both the longitudinal and transverse directions, in order to form a bowl-shaped space around the acquisition zone 112 of the sanitary napkin. Similar to the sanitary napkin in FIGS. 1 and 2, a number of different types of elastic means can be used to achieve the desired bending of the upper part.

At the rear part 104 of the upper part 101, a compression line 126 is arranged along the longitudinal centre-line 110 of the sanitary napkin. The compression line 126 serves as a fold line when the sanitary napkin is used and allows the rear part 104 to adopt a V-shaped cross-section, where the point of the V is facing towards the user, when the upper part is pressed together in the transverse direction between the thighs of the user. In this manner, the rear part of the upper part passes in between the buttocks of the user and serves as a barrier against rearward leakage of fluid.

Figure 4:
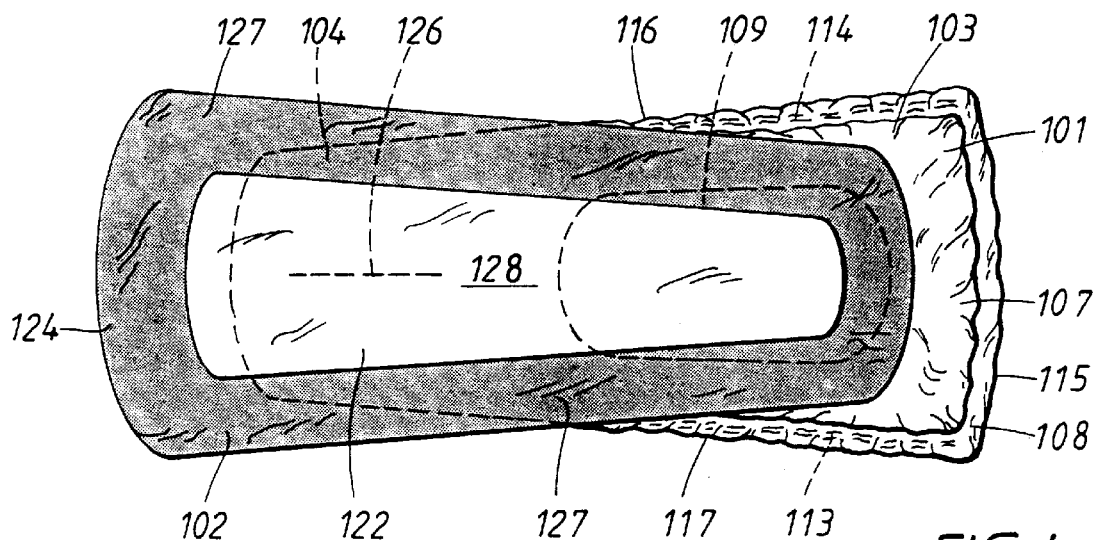
FIG. 4 shows the sanitary napkin of FIG. 1 seen from the side facing away from the user during use.

The lower part 102 of the sanitary napkin is made of a liquid impermeable layer 122, on the side which during use is facing towards the user, and has an absorption body 120 comprising a layer of an absorbent non-woven material on the side which is facing towards the upper part 101. No special surface layer is required over the absorbent non-woven layer. The lower part 102 is intended to be fastened in the crotch region of a pair of underpants by means of self-adhesive pressure sensitive glue 124, placed in a frame pattern along the edge parts 127 of the liquid impermeable layer 122 on the surface of the lower part 102 which during use faces towards the underpants of the user, as is shown in FIG. 4. By only fastening the lower part 102 along the edge parts 127, a certain freedom of movement between the middle part 128 of the lower part and the underpants perpendicular to the plane of the lower part is achieved. This can be an advantage since this permits good contact between the sanitary napkin 102 and the body of the user. This effect can be increased by means of a hump, 123, of absorbent material being arranged on the lower part 102, in the region for opening 109 in the absorption body 105 of the upper part 101 and the liquid impermeable covering layer 107. The hump 123 pushes up through the opening 109 in the upper part 101 and is covered by the liquid permeable covering layer 106 of the upper part. During use, the hump 123 lies against the body of the user and can, in this way, directly collect and absorb emitted body fluid.

The hump 123 is advantageously constructed from a soft resilient material, such as absorbent foam, absorbent fibre wadding, or cellulose pulp fluff mixed with thermoplastic fibres and thermo-bound to form a coherent, stable when moist, structure. It is, however, also possible to use any type at all of conventional absorption material. In order to achieve a high liquid retaining capacity in the lower part, this can contain super-absorbents, for example in the form of fibres or particles, preferably arranged in the hump. The absorbent non-woven material 120 can also, however, include a certain amount of super-absorbent, preferably in the form of super-absorbent fibres contained in the non-woven material. Such a super-absorbent contributes to immobilising fluid in the lower part 102 and in this way prevents the fluid being led out past the edges of the lower part through capillary forces in the non-woven material.

Figure 5:
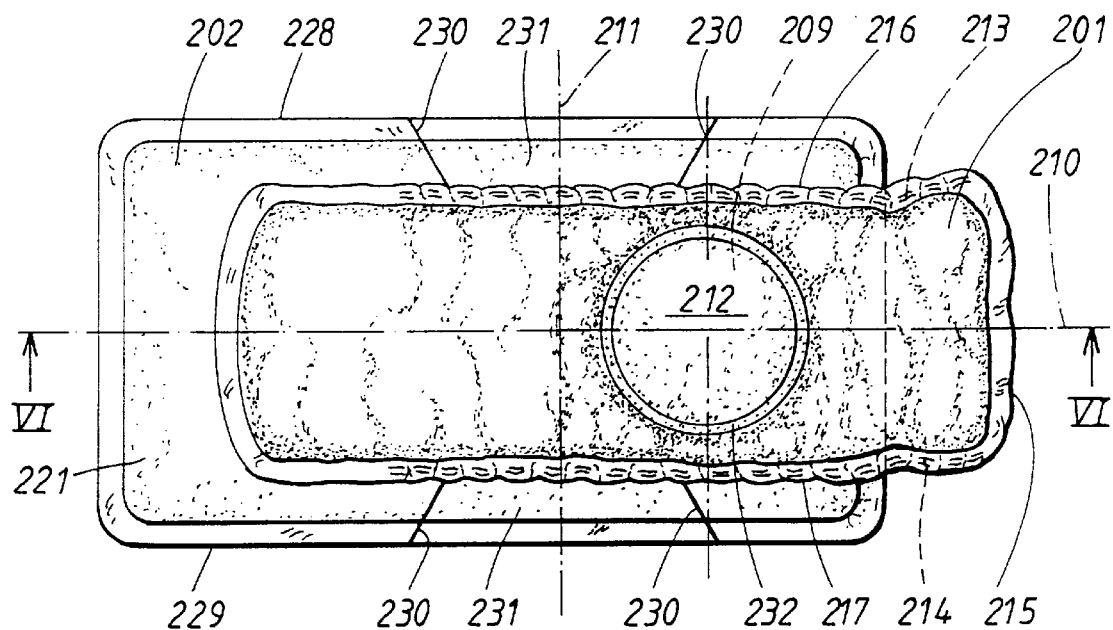
FIG. 5 shows yet another sanitary napkin shaped in accordance with the invention and seen from the side which is intended to be facing towards the user.
Figure 6:
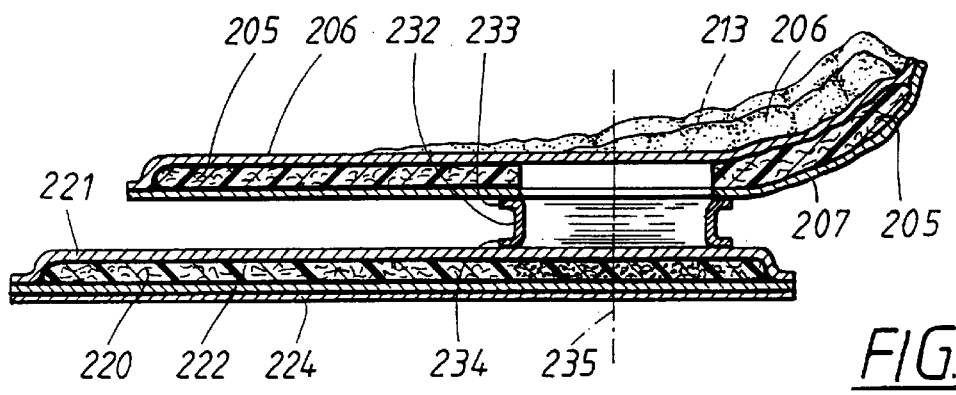
FIG. 6 shows a longitudinal cross-section along the line VI—VI through the sanitary napkin of FIG. 5.

The sanitary napkin shown in FIGS. 5 and 6 comprises an upper part 201 as well as a lower part 202 in the same way as the earlier described sanitary napkins. Both the upper part 201 and the lower part 202 have an absorption body 205, 220 enclosed between two covering layers 206, 207, 221, 222. The upper part 201 further comprises elastic means 213, 214 arranged along the two longitudinal side edges 216, 217, from the front cross edge 215 of the upper part, and extending out along approximately ⅔ of the length of the side edges 216, 217. The elastic means 213, 214 are attached in a pre-tensioned condition by glueing, welding or any other means so that they serve to bend the upper part 201 of the sanitary napkin along its longitudinal centre-line 210, when the pre-tension is released.

The liquid impermeable covering layer 222 of the lower part 202 is equipped with fastening means in the form of longitudinally extending strings of glue. In order to ensure good fastening of the lower part 202 in the underpants of the user, a string of glue is arranged near each longitudinal side edge 228, 229 on the lower part, and a glue string 224 is arranged along the longitudinal centre-line 210 of the sanitary napkin. Only the string of glue along the longitudinal centre line 210 is visible in the cross-section in FIG. 6. The lower part 202 is further comparatively wide, in order to be sure of covering the crotch part of underpants of different sizes. Oblique notches or cuts 230 are arranged two to each side edge 228, 229, approximately symmetrically on both sides of transverse centre line 211 of the sanitary napkin. These cuts 230 allow the parts 231 of the lower part lying between the cuts to form flaps which can be folded around the edges of the underpants of the user, in the case that the crotch of the panties in this region is narrower than the lower part 202 of the sanitary napkin. Such an arrangement, on the one hand, permits the sanitary napkin to sit most securely in position in the underpants and, on the other hand, ensures that the side edges of the underpants are extremely well protected against soiling by body fluid.

The two parts 201, 202 comprised in the sanitary napkin are mutually connected through a generally cylinder-shaped element 232 of flexible, preferably elastically stretchable, naterial. The cylinder-shaped element 232 is arranged so that its central axis 233 is orientated essentially perpendicular to the plane of the sanitary napkin, and extends between the liquid impermeable covering layer 207 of the upper part 201 and the liquid permeable covering layer 221 of the lower part 202. In the figures, the cylinder-shaped element 232 has been shown, for the sake of clarity, as a tube wtih straight smooth sides. In reality, however, the cylinder-shaped element 232 is in the normal case collapsed and folded together like a concertina.

The diameter of the cylinder-shaped element corresponds to the diameter of an opening 209 through the upper absorption body 205 and the liquid impermeable covering layer 207 of the upper part 201. The cylinder-shaped element 232 has flange-shaped parts 233, 234 around its two ends. At one end, the flange-shaped parts 233 are fastened to the liquid impermable covering layer 207 of the upper part 201 around the periphery of the opening 209. At the other end, the flange-shaped parts 234 are fastened against the liquid permeable covering layer 221 of the lower part 202. In a similar fashion to the earlier described embodiments, the fastening together of the different components can take place in a conventional manner, by means of glueing, sewing or welding. The placement of the cylinder-shaped element 232 coincides in the main with the acquisition zone 212 of the sanitary napkin.

The cylinder-shaped element 232 is preferably compressible along its central axis 235 and, in this condition, contributes only in the slightest degree to the total thickness of the sanitary napkin in the acquisition zone 212. Suitable materials for the cylinder-shaped element are preferably elastically stretchable non-woven tubes, or tubing, tubes of elastic foam, or rubber. Non-elastic non-woven material and knitted, woven or plaited elastic or non-elastic tubular-shaped structures can be used within the scope of the invention.

The purpose of the cylinder-shaped element 232 is to increase the mobility between the two parts 201, 202 comprised in the sanitary napkin, and to reduce the forces which are transferred between the parts. This mobility is achieved through the cylinder-shaped element 232 being deformable and able to be stretched, twisted and folded or compressed. In the embodiment shown in FIGS. 5 and 6, the cylinder-shaped element 232 furthermore serves as a fluid transferring means between the upper part and the lower part.

In order to be able to absorb the body fluid transferred through the cylinder-shaped element 232, the lower absorption body 220 comprises super-absorbents in the region of the cylinder-shaped element 220. In FIG. 6, the super-absorbents are shown as particles mixed in the lower absorption body 220. The super-absorbents can naturally be present in any other suitable form.

In the drawings, the thickness of the different components has been greatly exaggerated so that the construction of the different products should be easily seen. In reality, the total thickness of a product according to the invention is appropriately between approximately 1–5 mm at the ends of the product and approximately 5–15 mm at the acquisition zone.

The invention shall not be considered to be limited to the embodiments shown here but also a series of further embodiments are conceivable within the scope of the appended claims. The invention has been described in connection with sanitary napkins, but can naturally also be used for all types of absorption products which are intended to be fastened in a pair of underpants and to be held in contact against the body of the user with help of the underpants.

An example of such absorbent products incontinence protectors intended to be worn by lightly incontinent people. Because of the two-piece construction of a product according to the invention, it is possible to manufacture anathomically shaped incontinence protectors for men as well as for women, which sit securely and comfortably in place in the underpants of the user and at the same time give excellent protection against the leakage of fluid.

Individual features of the different described embodiments can naturally be arbritarily combined with the scope of the invention.

What is claimed is:

1. Absorbent product intended during use to be placed in a crotch region of a user in order to collect and absorb discharged body fluids, which product has a principally elongated shape with a longitudinal centre-line and a transverse centre line and comprises an upper part comprising absorbent material and intended during use of the product to be facing towards the user, and a lower part comprising absorbent material and intended during use of the product to be facing away from the user, said lower part having means for fastening inside a pair of underpants, wherein the two parts are mutually connected by a connection which enables the transfer of fluid between the two parts at the connection and the two parts have each a front part intended during use of the product to be facing forwardly and a rear part intended during use to be facing rearwardly the upper part and the lower part being mutually joined only at an acquisition zone of the product, which is the region of the product which is intended to first be wetted by bodily fluid, whereby the upper part outside the acquisition zone is free from connections to the lower part, thereby permitting both the front part and the rear part of the upper part to separate from the lower part.

2. Product according to claim 1, wherein the upper part and the lower part are mutually displaced along the longitudinal centre-line of the product, so that the front part of the upper part extends beyond the front part of the lower part, while the rear part of the lower part extends beyond the rear part of the upper part.

3. Product according to claim 1, wherein the front part of the upper part of the product has a transverse front edge and means for providing elasticity along the transverse front edge.

4. Product according to claim 1, wherein the upper part has longitudinal side edges and means for providing elasticity arranged along the longitudinal side edges of the upper part at the front part of the upper part.

5. Product according to claim 1, wherein the upper part comprises a first side which during use of the product is intended to be facing towards the user, the first side having a liquid permeable covering layer, a second side which during use of the product is intended to be facing towards the lower part, the second side having a liquid barrier covering layer, and an absorbent body contained between the two covering layers, wherein at least one through-opening is arranged in the liquid barrier covering layer at the acquisition zone of the product.

6. Product according to claim 5, wherein the at least one through-opening arranged in the liquid barrier covering layer also extends through the absorbent body in the upper part.

7. Product according to claim 5, wherein the liquid barrier covering layer of the upper part is permeable to body fluids at the rear part of the upper part, but is impermeable to body fluids at the front part of the upper part.

8. Product according to claim 5, wherein a hump of absorbent material is arranged on the lower part and extends up through the through-opening in the liquid barrier covering layer of the upper part.

9. Product according to claim 1, wherein the means for fastening of the product inside a pair of underpants is made up of a coating of pressure sensitive, self-adhesive glue.

10. Product according to claim 9, wherein the lower part has a surface which during use is facing away from the user, and the adhesive coating covers the whole of the surface of the lower part which during use of the product is facing away from the user.

11. Product according to claim 9, wherein the lower part has a surface which during use is facing away from the user, and the adhesive coating is arranged along edges of the surface of the lower part which surface during use of the product is facing away from the user.

12. Product according to claim 1, wherein the upper part has a relatively wide front part and a relatively narrower rear part.

13. Product according to claim 1, wherein the lower part has a relatively narrow front part and a relatively wider rear part.

14. Product according to claim 12, wherein the upper part is spoon-shaped.

15. Product according to claim 1, wherein the rear part of the upper part has a hump shaped so that during use of the product it fits in a furrow between the buttocks of the user behind the genitals.

16. Product according to claim 15, wherein the hump is drop-shaped.

17. Product according to claim 1, wherein the rear part of the upper part has a fold guide, which when the product is subjected to compressive transverse forces during use, causes the rear part of the upper part to adopt, in cross-section, the shape of a V, with the point of the V directed towards the user.

18. Product according to claim 1, wherein the connection between the upper part and the lower part is elastically stretchable.

19. Product according to claim 1, wherein the rear part of the lower part has a transverse raised edge of liquid barrier material.

20. Product according to claim 1, wherein the lower part has side edges, and two principally transverse notches or cuts are arranged on each side edge on the lower part, approximately symmetrically on both sides of the transverse centre line of the product, thus forming parts of the lower part lying between the notches or cuts, said parts being intended to be folded around the edges of the pair of underpants of the user.

21. The product of claim 1 wherein the absorbent product is one of a sanitary napkin, a panty liner, or an incontinence protector.

* * * * *